United States Patent [19]

Sandvig et al.

[11] Patent Number: 4,946,726
[45] Date of Patent: * Aug. 7, 1990

[54] ORTHOPEDIC SPLINTING ARTICLES AND METHODS

[75] Inventors: Timothy C. Sandvig, Woodville, Wis.; Dennis C. Bartizal; Matthew T. Scholz, both of Woodbury, Minn.

[73] Assignee: Minnesota Mining and Manufacturing Company, St. Paul, Minn.

[*] Notice: The portion of the term of this patent subsequent to Aug. 4, 2004 has been disclaimed.

[21] Appl. No.: 15,972

[22] Filed: Feb. 18, 1987

Related U.S. Application Data

[63] Continuation-in-part of Ser. No. 784,345, Oct. 4, 1985, Pat. No. 4,683,877.

[51] Int. Cl.$^5$ ............................................. A61F 5/04
[52] U.S. Cl. ................................. 428/76; 428/219; 428/308.4; 428/317.3; 428/317.7; 428/423.3; 428/913; 128/90
[58] Field of Search ............... 128/90; 428/219, 308.4, 428/317.3, 317.7, 423.3, 913, 76, 542.8; 206/389, 438, 440

[56] References Cited

U.S. PATENT DOCUMENTS

| | | | |
|---|---|---|---|
| 1,914,049 | 6/1933 | Smith | 128/595 |
| 2,759,475 | 8/1956 | Van Swaay | 128/90 |
| 2,800,129 | 7/1957 | Van Swaay | 128/90 |
| 2,973,529 | 3/1961 | Silverman | 128/595 |
| 3,040,740 | 6/1962 | Parker | 128/83 |
| 3,048,169 | 8/1962 | Pierce | 128/90 |
| 3,301,252 | 1/1967 | Mahoney, Jr. | 128/90 |
| 3,320,347 | 5/1967 | Greenawalt | 128/595 |
| 3,373,741 | 3/1968 | Hill et al. | 128/90 |
| 3,375,822 | 4/1968 | Rose | 128/90 |
| 3,572,330 | 3/1971 | Gander | 128/90 |
| 3,608,238 | 9/1971 | Reuter | 47/64 |
| 3,656,475 | 4/1972 | Hanrahan | 128/90 |
| 3,728,206 | 12/1973 | Buese | 161/112 |
| 3,799,755 | 3/1974 | Rack | 47/56 |
| 3,819,796 | 6/1974 | Webster et al. | 264/321 |
| 3,847,722 | 11/1974 | Kistner . | |
| 3,889,417 | 6/1975 | Wood et al. | 47/56 |
| 3,900,024 | 8/1975 | Lauber et al. | 128/91 R |
| 3,935,355 | 1/1976 | Kuhn | 128/90 |
| 3,985,128 | 10/1976 | Garwood et al. | 128/90 |
| 3,998,219 | 12/1976 | Mercer et al. | 128/89 |
| 4,019,506 | 4/1977 | Eschmann | 128/90 |
| 4,060,075 | 11/1977 | Blomer et al. | 128/90 |
| 4,083,127 | 4/1978 | Hanson | 36/93 |
| 4,144,658 | 3/1979 | Swan, Jr. | 36/117 |
| 4,182,056 | 1/1980 | Dalebout | 36/117 |
| 4,193,395 | 3/1980 | Gruber | 128/90 |
| 4,211,019 | 7/1980 | McCafferty | 36/43 |
| 4,232,457 | 11/1980 | Mosher | 36/44 |
| 4,235,228 | 11/1980 | Gaylord, Jr. et al. | 128/91 |
| 4,245,410 | 1/1981 | Molitor | 36/117 |
| 4,255,202 | 3/1981 | Swan, Jr. | 106/122 |
| 4,280,489 | 7/1981 | Johnson, Jr. | 128/80 H |
| 4,301,564 | 11/1981 | Dalebout | 12/146 R |
| 4,309,990 | 1/1982 | Brooks et al. | 128/90 |

(List continued on next page.)

FOREIGN PATENT DOCUMENTS 0223380 5/1987 European Pat. Off. .
83/01736 5/1983 PCT Int'l Appl. .

Primary Examiner—James C. Cannon
Attorney, Agent, or Firm—Donald M. Sell; Walter N. Kirn; Dale E. Husle

[57] ABSTRACT

The present invention relates to orthopedic splinting articles and methods for forming orthopedic splints at least part way around an animal body part. The splinting articles comprise a unitary blank formed of an open-celled foam sheet impregnated with a water curable, isocyanate functional, polyurethane prepolymer resin. The blank is dimensioned to extend the length of the body part to be immobilized and to partially, but preferably not completely, extend around the circumference of the body part. Upon activation of the resin impregnated foam sheet and molding the same around the body part, an orthopedic splint is formed.

35 Claims, 3 Drawing Sheets

U.S. PATENT DOCUMENTS

| | | | |
|---|---|---|---|
| 4,323,061 | 4/1982 | Usukura | 128/90 |
| 4,325,380 | 4/1982 | Malkin | 128/581 |
| 4,331,134 | 5/1982 | Brooks et al. | 128/90 |
| 4,346,525 | 8/1982 | Larsen et al. | 36/69 |
| 4,347,213 | 8/1982 | Rogers, Jr. | 264/510 |
| 4,370,976 | 2/1983 | Wanchik et al. | 128/77 |
| 4,376,438 | 3/1983 | Straube et al. | 128/90 |
| 4,411,262 | 10/1983 | von Bonin et al. | 128/90 |
| 4,414,762 | 11/1983 | Salomon et al. | 36/117 |
| 4,419,261 | 12/1983 | Takahashi | 252/182 |
| 4,433,680 | 2/1984 | Yoon | 128/90 |
| 4,439,934 | 4/1984 | Brown | 36/44 |
| 4,442,833 | 4/1984 | Dahlen et al. | 128/90 |
| 4,450,833 | 5/1984 | Brooks et al. | 128/90 |
| 4,451,310 | 5/1984 | Lairloup | 156/78 |
| 4,470,782 | 9/1984 | Zimmerman, Jr. et al. | 425/2 |
| 4,502,479 | 3/1985 | Garwood et al. | 128/90 |
| 4,510,700 | 4/1985 | Brown | 36/44 |
| 4,520,581 | 6/1985 | Irwin et al. | 36/88 |
| 4,522,777 | 6/1985 | Peterson | 264/223 |
| 4,565,250 | 1/1986 | Vasko | 168/12 |
| 4,597,196 | 7/1986 | Brown | 36/44 |
| 4,609,578 | 9/1986 | Reed | 428/76 |
| 4,628,621 | 12/1986 | Brown | 36/44 |
| 4,638,795 | 1/1987 | Richter et al. | 128/90 |
| 4,667,661 | 5/1987 | Scholz et al. | 128/90 |
| 4,683,877 | 8/1987 | Ersfeld et al. | 428/317.3 |
| 4,705,840 | 11/1987 | Buckanin | 528/53 |

ORTHOPEDIC SPLINTING ARTICLES AND METHODS

RELATED APPLICATIONS

This application is a continuation-in-part of application Ser. No. 784,345, filed Oct. 4, 1985 for "Orthopedic Casting Article and Method (now U.S. Pat. No. 4,683,877)" which application is incorporated herein by reference.

BACKGROUND

1. The Field of the Invention

The present invention relates to orthopedic splints. In particular, this invention relates to orthopedic splinting materials and methods utilizing an open-celled foam sheet impregnated with a water curable resin. Such articles and methods are particularly suited for providing temporary splints around fresh fractures where significant swelling is expected.

2. The Prior Art

Severe injury to body limbs, particularly injuries involving a fresh fracture of the bone or damage to the soft tissue suporting the bone, are frequently treated by temporarily immobilizing the injured limb with a splint until swelling has abated. After such time, the splint may then be removed and a rigid cast applied. Because a temporary splint must allow for swelling of the limb, the splint generally should not encompass the entire limb so as to better accommodate expansion of the limb. Many different systems have been devised for providing orthopedic splints.

For example, U.S. Pat. Nos. 2,759,475 and 2,800,129 disclose blanks for forming splints comprising a solid thermoplastic material provided on one surface with a foam plastic layer. The blank is heated to a temperature such that the solid thermoplastic material becomes soft, and is then applied to the body part and shaped to form the splint.

Similarly, U.S. Pat. No. 4,442,833 discloses a casting or splinting bandage comprising a closed-cell polymer foam and a plurality of sheets of a textile material impregnated with a water curable resin.

U.S. Pat. No. 4,235,228 discloses an orthopedic material comprising a plaster impregnated fabric core, a layer of padding around at least one surface of the fabric, and a length of tubular stockinet encircling the fabric and padding. This combination can be cut to a desired length, dipped in water to begin hardening of the plaster, attached to a patient by a bandage or other fastener, and allowed to harden to form a splint.

The systems described in U.S. Patent Nos. 4,442,833 and 4,235,228 are relatively damp when applied, and can thus provide undesirable environments for any wounds present and/or promote skin maceration on those body parts over which the splints are applied.

U.S. Pat. No. 3,985,128 discloses a splint that can be applied dry, but ultraviolet light is required to harden the splint. Thus, such a splint can only be used where a source of ultraviolet light is available. U.S. Pat. No. 3,728,206 describes a foam impregnated with a thermoplastic resin.

U.S. Pat. No. 4,411,262 discloses a constructional material comprising a flexible substrate impregnated or coated with a resin system which is cured by air moisture. In one embodiment, the flexible substrate may be a foam which is resin impregnated by solvent coating onto the foam an isocyanate sump residue which has a viscosity between 3,000 and 50,000 centipoise.

U.S. Pat. No. 4,628,917, which issued on Dec. 16, 1986 and which is assigned to the same assignee as the present invention, discloses a combination of materials that can be used to form a splint or protective covering, including a support mat comprising a flexible fabric impregnated with a water curable resin with a water restricting film along at least one of its major surfaces, and a pressure sensitive adhesive coated padding that can be adhered to the support mat after the fabric is exposed to water so that the resultant laminate can be applied to a person with the dry surface of the padding against the person's skin.

In selecting suitable materials for forming orthopedic splints, the prior art has encountered several problems. First, it has been sought to use a low viscosity resin which may be easily coated upon the supporting fabric or material to be used in the splint. However, splints prepared from such low viscosity resins, when formulated to give a proper set time, typically result in unacceptably high exotherms, which can result in burning the patient. High viscosity resins, on the other hand, typically require complicated techniques for application, such as solvent coating the resin onto the fabric or substrate. Further, the fabrics or scrim materials used in such splints have typically been relatively inextensible in order to provide sufficient strength for the resulting splint; however, the result is a splinting material which has poor extensibility and which thus does not conform well to the body part to which it is applied. Finally, if the splinting materials used in the prior art do not exhibit sufficient water vapor permeability, skin maceration can result.

From the foregoing, it will be appreciated that what is needed in the art is improved orthopedic splinting materials which have acceptable setting times and exotherms without the need for complicated resin application techniques, and which avoid the problems of the prior art set forth above. Such splinting materials and methods for applying such splinting materials are disclosed and claimed herein.

BRIEF SUMMARY OF THE INVENTION

The present invention relates to an article which is suitable for forming an orthopedic splint around a portion of an animal body part, which splinting article avoids the problems of the prior art. The article of the present invention greatly simplifies splint application.

According to a presently preferred embodiment of the invention, a unitary blank is provided which comprises a pliant, extensible, and highly conformable substrate. The blank is dimensioned in a first direction sufficient to extend the length of the body part and is dimensioned in a second direction sufficient to extend partially, but preferably not completely, around the circumference of the body part. In this regard, the blank is dimensioned in the second direction so as to envelop the body part to the extent that is needed to support and immobilize the body part, while still accommodating for the swelling which generally occurs as a result of a fresh fracture or soft tissue injury.

Importantly, the blank comprises an open-celled foam sheet and a water curable, isocyanate functional, prepolymer resin impregnated into the open-celled foam sheet. The prepolymer resin is a polyurethane resin formed by reacting a polyisocyanate with a polyol, preferably while the polyisocyanate and the polyol are inside the open-celled foam sheet. The ratio of isocyanate (NCO) groups in the polyisocyanate to hydroxyl (OH) groups in the polyol is about 2:1 to about 3.5:1. The isocyanate equivalent weight in the resultant prepolymer is from about 350 grams to about 1000 grams of prepolymer per isocyanate group. The orthopedic splint is formed by activating the polyurethane prepolymer resin and applying the blank around the portion of the body part to be splinted and immobilized.

The strength and rigidity of the cured splint are dependent primarily upon the rigidity of the cured prepolymer resin rather than the initially flexible open-celled foam sheet. By maintaining the NCO:OH ratio and isocyanate equivalent weight within the ranges disclosed herein, safe levels of heat generated during cure are maintained, while providing a cured resin having the rigidity needed.

Because the polyisocyanate and polyol are preferably not prereacted, but are rather reacted while within the foam sheet to form the polyurethane prepolymer resin, it is possible to select and employ a prepolymer resin which is more highly viscous than the resins used in the prior art. In this regard, reacting the prepolymer components within the foam sheet itself avoids the necessity of trying to solvent-coat the resultant viscous prepolymer resin or of finding some other method of applying the viscous resin. Surprisingly, the high viscosity prepolymer resins employed in the present invention have good set times, relatively low exotherms, and sufficient rigidity to be useful in supporting an injured body part.

Furthermore, because the foam sheet itself is pliant, extensible, and highly conformable, and because the use of a rigid or stiff scrim which would otherwise impair extensibility is avoided, the extensibility of the resin impregnated foam is quite good. The reason that a rigid scrim is not needed in the present invention is that, surprisingly, the foam sheet alone can be resin loaded to a very high degree and thereby impart the strength necessary to form a suitable orthopedic splint. Also surprisingly, after resin loading the foam sheet to the extent necessary to achieve the desirable degree of strength, the resultant splint still exhibits good water vapor permeability so as to substantially avoid skin maceration.

Because an extra scrim is not needed with the resin impregnated foam sheet, good conformability and moldability and omnidirectional extensibility in applying the splint are made possible. As a result, good alignment of the splint with respect to the body part can be achieved. Another surprising benefit of the present invention is that the surface of the resin impregnated foam sheet is surprisingly less tacky than would be expected (especially at such high resin loadings), thereby greatly facilitating application of the splint.

In summary, the present invention provides a one piece article which may be formed, using solventless techniques, into an orthopedic splint having the following desirable benefits during application: good conformability and moldability, omnidirectional extensibility, good alignment of the splinting material, low exotherm, relatively short cure times, reduced tack, and good resin loading. Upon curing, the resultant splint exhibits good strength and good water vapor permeability.

These and other objects and features of the present invention will become more fully apparent from the following description and appended claims, taken in conjunction with the accompanying drawings.

DETAILED DESCRIPTION OF THE PREFERRED EMBODIMENTS

The subject matter of the present application is a continuation-in-part of the subject matter of copending application Ser. No. 784,345, filed Oct. 4, 1985, for "Orthopedic Casting Article and Method (now U.S. Pat. No. 4,683,877) ". Application Ser. No. 784,345 (now U.S. Pat. No. 4,683,877) discloses an orthopedic casting article and method for forming an orthopedic cast around an animal body utilizing a unitary blank which comprises a pliant, extensible layer of a foam member, an extensible fabric bonded to the foam member, and a curable resin impregnatably associated with the foam member.

The subject matter of the present application is directed to an orthopedic splinting article and method for forming an orthopedic splint part way around an animal body part, and utilizes some of the principles disclosed in application Ser. No. 784,345 (now U.S. Pat. No. 4,683,877) orthopedic splinting article of the present invention utilizes a sheet of foam impregnated with a curable resin; however, no extensible fabric is bonded to the foam sheet prior to its application as a splint. Other features and parameters have been discovered and carefully tailored such that a resin impregnated foam sheet itself may be used effectively as an orthopedic splint.

For example, in the present invention, it has been discovered that a relatively soft, low density, highly flexible foam sheet can be impregnated with sufficient resin to render the impregnated foam rigid enough to function as an orthopedic splint, yet maintain safe exotherm during cure and sufficient water vapor porosity after cure so that skin maceration is substantially avoided. Reference will now be made to the drawings wherein like parts are designated with like numerals throughout.

Figures 1, 2A:
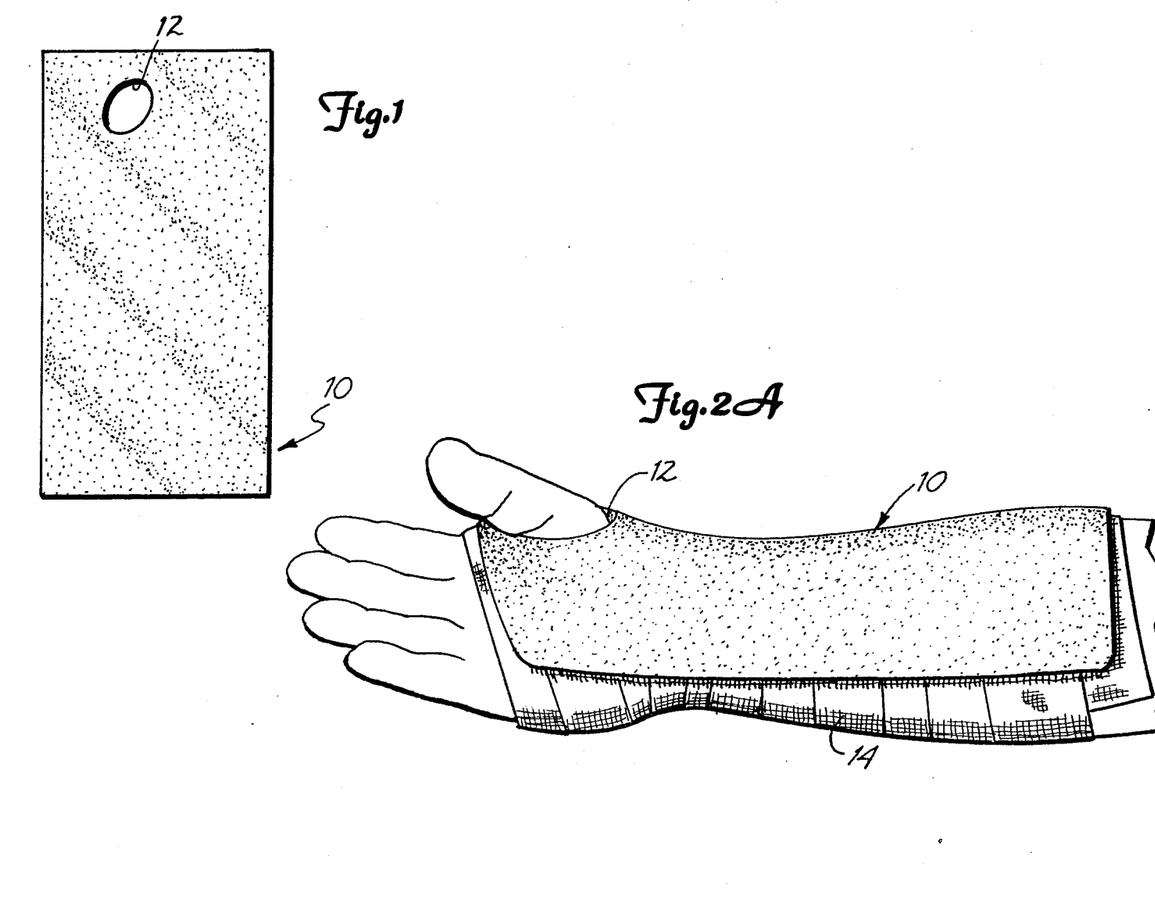
FIG. 1 is a plan view of a preferred forearm embodiment of the orthopedic splinting article of the present invention prior to application.
FIG. 2A is a perspective view of one side of the orthopedic splinting article of FIG. 1 which has been trimmed to fit and formed into a forearm splint.
Figure 2B:
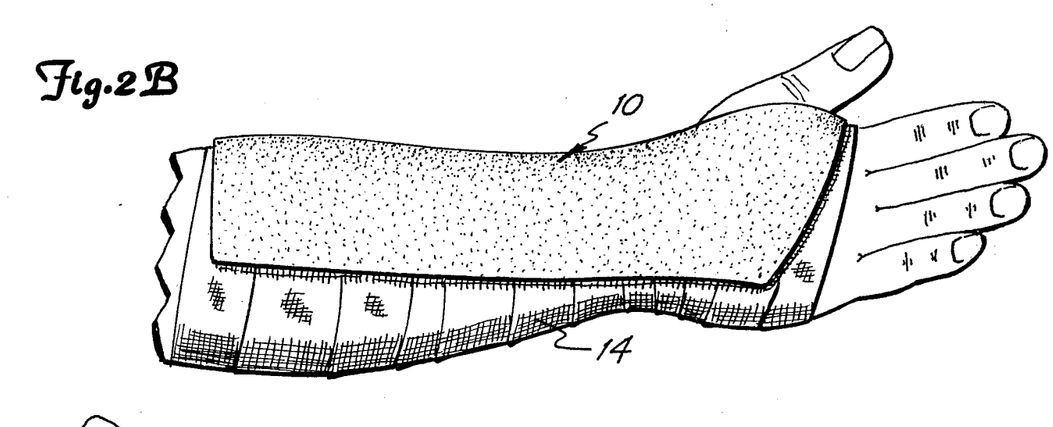
FIG. 2B is a perspective view of the opposite side of the orthopedic splinting article shown in FIG. 2A.

Referring now to FIG. 1, there is shown in plan view a preferred forearm orthopedic splinting article 10 of the present invention in the form of a unitary blank. The article or blank 10 is generally comprised of a pliant, extensive layer or sheet of a foam member, and preferably has a thumbhole 12 formed therein to facilitate application of the article 10 around a wearer's forearm as shown in FIG. 2. Article 10 of FIG. 1 is initially configured as a rectangle, and is then trimmed to custom fit the patient as shown in FIGS. 2A and 2B. In this regard, the physical characteristics of the foam material allow for easy trimming without leaving rough edges.

The foam sheet of article 10 is open-celled, and a curable resin is impregnatably associated with the foam sheet. As used herein, the term "open-celled" refers to a foraminous structure having interconnecting or communicating orifices or cavities therein caused by a sufficient number of the wall membranes of the foam cells having been removed to allow impregnation of the foam sheet 10 with an effective amount of the resin so that an efficacious splint can be formed. Further, as used herein, the term "impregnated" refers to the condition in which the resin is thoroughly intermingled with and in surrounding relation to the wall membranes of the cells and the interconnected cell frame members of the foam sheet 10.

The foam sheet of article 10 can comprise any one of a number of extensible foams which are open-celled, such as polyether or polyester based polyurethane foams. Importantly, the porosity of the foam sheet 10 must be such that it can be resin loaded sufficiently to provide a satisfactory orthopedic splint. In this regard, the open-celled foam sheet preferably has from about 30 to about 120 pores per inch. As used herein, the term "pores per inch" refers to the average number of pores located along a linear inch of the foam sheet. The number of pores per linear inch may be determined, for example, by measuring the foam's resistance to air flow or a pressure differential and using such information to calculate the approximate number of pores in the foam.

When the pores per inch value is decreased below 30, the foams become too course or rough, and typically do not hold enough resin to provide the necessary strength for the resulting orthopedic splint. Foam sheets having over about 100 pores per inch are not known to be presently commercially available. It will be understood, however, that the upper limit for the pores per inch parameter is limited solely by the ability to resin load the foam sheet to the extent needed to provide sufficient strength for an orthopedic splint, while still maintaining adequate porosity. Since foam sheets having over 100 pores per inch are not presently available, it is difficult to currently predict the performance of foams having substantially greater than 100 pores per inch as to their resin loading characteristics and porosity. Thus, in the most presently preferred embodiment of the present invention, the open-celled foam sheet used to form article 10 has from about 45 to about 100 pores per inch.

Foam sheet thicknesses of between about 5/16 of an inch to about ¾ of an inch are presently preferred, with a foam sheet thickness of about ½ inch being most presently preferred. Foam sheets much less than about 5/16 of an inch in thickness are generally too thin to yield a splinting article of sufficient strength at the maximum possible resin loading. Foam sheet thicknesses much greater than about ¾ of an inch tend to be too cumbersome and bulky for the patient and are aesthetically unpleasing. Furthermore, such thicker foam sheets may undesirably increase the exotherm felt by the patient during resin cure due to the increased insulative value of the thicker foam.

Figure 3:
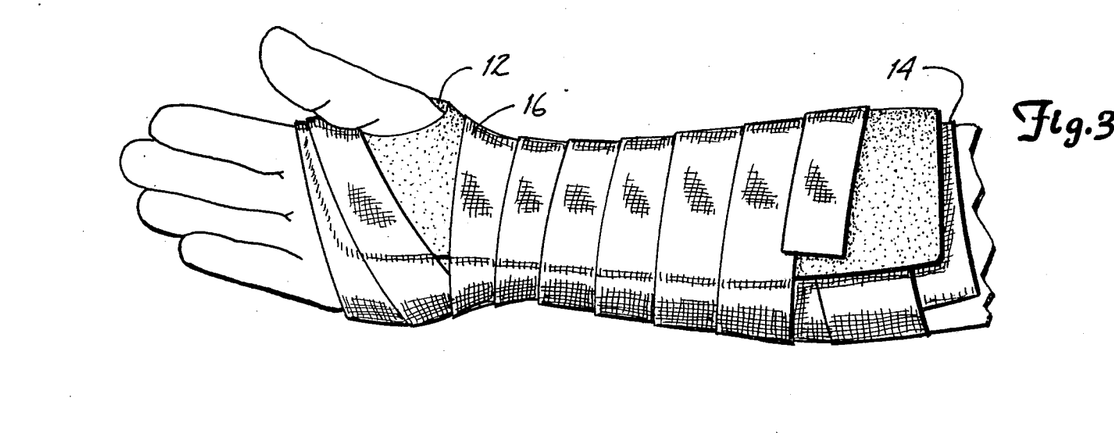
FIG. 3 is a perspective view of the embodiment of FIG. 2A additionally showing a stretch bandage which may be optionally wrapped around the splinting article in order to provide better conformability and attachment of the splinting article to the forearm.

For the forearm splint embodiment of FIGS. 1-3, a foam sheet approximately 7 inches wide, 12 inches long, and ½ inch thick is presently preferred. For the lower leg embodiment of FIGS. 4-5, a foam sheet approximately 10 inches wide, 38 inches long, and about ½ inch thick is presently preferred. However, it will be appreciated that the exact dimensions employed may vary according to the respective limb sizes of the individual to be treated.

The foam sheet utilized in article 10 preferably has a density in the range of about 1 to about 4.5 pounds per cubic foot, and most preferably, between about 1 and about 3 pounds per cubic foot. Foam sheets possessing densities lower than about 1 pound per cubic foot are not known to be presently commercially available. Foam sheets having densities higher than about 4.5 pounds per cubic foot tend to preclude the resin loading which is necessary to achieve proper splint strength.

One presently preferred material for the foam sheet of the present invention is a polyether based polyurethane foam sheet that is ½ inch thick and is presently available from Illbruck U.S.A., Minneapolis, Minn., as type E-150. It has been found that this foam material, when impregnated with a resin in accordance with the present invention, will provide a splint of sufficient strength and air permeability to be efficacious.

The presently most preferred resins for impregnating the foam sheet materials of the present invention are water curable, isocyanate functional, polyurethane prepolymers prepared by the reaction of a polyol with an excess of a polyisocyanate. The presently preferable polyurethane prepolymer resins have a relatively high viscosity. In this regard, after choosing an appropriate polyol and polyisocyanate to form the polyurethane prepolymer resin, the resultant prepolymer has a viscosity of at least about 75,000 centipoise or greater, and the presently most preferable embodiments of the present invention exhibit a viscosity of about 100,000 centipoise or greater.

It will be understood that the above viscosity values and all others set forth herein are values taken at room temperature (about 23° C.) and after a period of 24 hours following reaction of the polyol with the polyisocyanate. Further, all viscosity values set forth herein were measured using a Model RVT viscometer obtained from Brookfield Engineering Lab., Stoughton, Mass. 02072 equipped with spindle #6 (or spindle #7 in the case of viscosities greater than 100,000 centipoise) set at a rotational rate of 10 revolutions per minute (10 rpm). Thus, the viscosity values and ranges set forth herein necessarily relate to the viscosities which would be measured using such an apparatus and conditions; other apparatus and conditions may well provide other viscosity values.

The most important factors in the choice of an appropriate polyol and an appropriate polyisocyanate to form the polyurethane prepolymer resin are the NCO:OH ratio, that is, the number of isocyanate (NCO) groups in the polyisocyanate as compared to the number of hydroxyl (OH) groups in the polyol, and the NCO equivalent weight of the prepolymer. When these two parameters are controlled as taught herein, a splint can be formed having: (1) sufficient rigidity to immobilize a body member such that undesired movement, which would disturb or compromise the immobilized area, is substantially prevented, and (2) low enough exotherm to permit application to the body member without undesirably high levels of heat being liberated. In fact, in the presently preferred embodiments of the present invention, the exotherms are such that temperatures of 48° C. or less are felt by the patient, with temperatures of about 40° C or less being felt by the patient in the most presently preferred embodiments.

In accordance with the foregoing, the NCO:OH ratio of the reactants must be within the range of about 2:1 to about 3.5:1, and preferably within the range of about 2.5:1 to about 3.0:1. It has been found that NCO:OH ratios lower than about 2:1 do not provide enough excess isocyanate groups to achieve adequate crosslinking of the resin during cure, while NCO:OH ratios greater than about 3.5:1 tend to produce undesirable exotherms (when industry standard isocyanate equivalent weights are used) which could potentially burn the patient.

Further in this regard, the isocyanate equivalent weight in the resultant prepolymer is preferably relatively large. The isocyanate equivalent weight is defined as the grams of prepolymer per NCO group. For purposes of the present invention, it has been found that the isocyanate equivalent weight should be within the range of about 350 grams to about 1000 grams of prepolymer per NCO group, and preferably within the range of about 370 grams to about 600 grams of prepolymer per NCO group. The average hydroxyl equivalent weight of the polyol before formation of the prepolymer, although less important, is generally about 200 grams to about 400 grams of polyol per OH group, and is about 220 grams of polyol per OH group in one very specific and presently preferred embodiment of the present invention.

Surprisingly, by using the relatively low NCO:OH ratios, relatively high isocyanate equivalent weights, and relatively high viscosity polyurethane prepolymers discussed herein, a low enough exothermic reaction can be achieved during cure to avoid burning the patient, even at high prepolymer resin content in the splint. At the same time, the rapid cure times and final rigidity needed for immobilization of the injured body member are also achieved.

The primary reason that such high viscosity polyurethane prepolymers (where the most preferable prepolymers have a viscosity of 100,000 centipoise or greater) may be employed in the present invention is that the polyol and polyisocyanate are preferably reacted in situ in the foam sheet, well before the final viscosity of 100,000 centipoise or greater is reached in the prepolymer product. In order to accomplish this, the polyol and polyisocyanate are mixed together, and the mixture is immediately squeezed or otherwise manipulated into the foam sheet so that the substantial portion of the polyol/polyisocyanate reaction takes place within the foam sheet itself. Alternatively, the polyol and polyisocyante could be independently squeezed into the foam sheet and mixed therein so as to react only upon their contact within the foam. Such procedures avoid the necessity of solvent coating the extremely viscous polyurethane prepolymer onto the foam sheet and the attendant disadvantage of having to subsequently remove the solvent, and the resultant resin impregnated foam sheet has relatively low exotherm and sufficient strength upon curing.

Although the in situ reaction technique outlined above is presently most preferred, there are other techniques, including additional solventless techniques, which could be used, if desired, to impregnate the prepolymer resin into the foam sheet. For example, it is also possible to first react the polyisocyanate and polyol to form the polyurethane prepolymer resin, heat the prepolymer resin to a temperature sufficient to significantly reduce its viscosity (for example, 60° C. or higher), immerse the foam sheet into the heated prepolymer resin, and squeeze the foam while thus immersed to impregnate the foam with the prepolymer resin. However, it should again be emphasized that the presently most preferable technique for impregnating the foam with the resin is by reacting the polyisocyanate and polyol in situ within the foam.

Surprisingly, the polyurethane prepolymer resin can be loaded into the foam sheets of the present invention so as to comprise from about 70% to about 95% by weight of the total article. Such a high degree of resin loading imparts to the cured article the necessary strength to function as an orthopedic splint. Also surprisingly, after loading such large percentages of resin into the foam, the resultant article has quite good water vapor permeability and porosity, thereby substantially avoiding skin maceration.

Examples of isocyanates used to form polyisocyanates which are suitable for purposes of the present invention are disclosed in U.S. Pat. Nos. 4,376,438, 4,433,680, and 4,502,479. Those isocyanates which are presently preferred include 2,4'-diphenylmethane diisocyanate, 4,4'-diphenylmethane diisocyanate, mixtures of these isomers together with possible small quantities of 2,2'-diphenylmethane diisocyanate (typically contained in commercially available diphenylmethane diisocyanates), and aromatic polyisocyanates and their mixtures such as are derived from phosgenation of the condensation product of aniline and formaldehyde. It is presently preferred to use an isocyanate which has low volatility such as diphenylmethane diisocyanate rather than a more volatile material such as toluene diisocyanate. Commercially available isocyanate starting materials include Isonate® 143L available from Upjohn, LaPorte, Tex., which is a mixture of isocyanate compounds containing about 73% by weight of diphenylmethane diisocyanate, and Mondur® MRS-10 available from Mobay Chemical Corp., New Martinsville, W. Va.

Examples of polyols which are suitable for purposes of the present invention include polyoxypropylene polyols, castor oil type triols, and polyester polyols. Specific polyols which are useful include polypropylene glycols such as PPG 425 and PPG 725 available from Union Carbide, Danbury, Conn., polypropylene triols such as LHT 240 available from Union Carbide, and castor oil polyols.

However, it will be understood that, as used herein, the term "polyol" also includes virtually any functional compound having active hydrogen in accordance with the well-known Zerevitinov test, as described, for example, in *Chemistry of Organic Compounds* by Carl R. Noller, Chapter 6, pp. 121–122 (1957). Thus, for example, thiols and polyamines could also be used as "polyols" in the present invention, and the term "polyols" will be considered to include such other active hydrogen compounds. In such instances, the NCO:active hydrogen ratio of the polyisocyanate to the active hydrogen compound used to form the polythiocarbamate, polyurea, or other polymer, should fall within the same ranges as disclosed herein for the NCO:OH ratios.

An especially preferred resin for use in the splint articles of the present invention includes the Modur® MRS-10 isocyanate available from Mobay Chemical, and a castor oil polyol available from Caschem, Bayonne, N.J. Another preferred resin may be formed by reacting Isonate® 143L and the polypropylene oxide polyol available from Union Carbide as Niax® polyol PPG 425. To prolong the shelf life of material, it is preferred to include about 0.02 to about 0.1 percent by weight of benzoyl chloride or other suitable stabilizer (e.g., an antioxidant such as butylated hydroxy toluene at a level of about 0.05 to about 0.25 weight percent).

Foaming of the resin which would reduce the porosity of the cured device and its overall strength should be minimized. Foaming occurs because carbon dioxide is released when water reacts with isocyanate groups. The most satisfactory method of minimizing foaming involves the addition of a foam suppressor such as silicone Antifoam A (Dow Corning, Midland, Mich.), DB-100 silicone fluid (Dow Corning), or silicone surfactants L550 or L5303 (Union Carbide) to the resin. It is presently preferred to use a silicone liquid such as Dow Corning DB-100 at a concentration of about 0.1 to about 1.0 percent by weight.

It is possible to make the curable resin of the present invention less tacky in accordance with the invention described in commonly assigned, copending U.S. patent application Ser. No. 784,671, filed Oct. 4, 1985, for "Curable Resin Coated Sheet Having Reduced Tack," filed in the name of Matthew T. Scholz et al. (now U.S. Pat. No. 4,667,661), which application is incorporated herein by reference. Reduced tackiness may be achieved by a number of means as described in application Ser. No. 784,671 (now U.S. Pat. No. 4,667,661), the result being that the kinetic coefficient of friction of the surface of the splinting article is less than about 1.2, when measured according to the procedure of ASTM-D-1894 with one slight modification which is within the scope of and contemplated by ASTM-D-1894. (This modification is that, instead of covering the test sled with a layer of the material to be tested as called for in the specific procedure spelled out in ASTM-D-)1894, the test sled was instead covered only with a layer of aluminum foil. One technique for achieving such tack reduction is to lightly spray the surfaces of the resin-impregnated article 10 with a mixture of a polydimethylsiloxane, having a viscosity of at least about 100 centistokes, and polyethylene oxide long chain aliphatic hydrocarbon waxes. Alternatively, a small amount of a polyethylene oxide-polypropylene oxide block copolymer may be added to the polyol during prepolymer preparation, after which the polydimethylsiloxane may be sprayed onto the surface of the article 10 as before. The polydimethylsiloxane reduces resin tackiness prior to contact with water. The hydrophilic polyethylene oxide materials provide additional tack reduction upon contact with water.

Reduced resin tack facilitates application of the splinting article 10 to the patient's limb. However, the orthopedic splinting articles of the present invention can be successfully applied without reducing tack. In this regard, it has been surprisingly found that the polyurethane resin impregnated foam articles of the present invention already experience much less tack than would normally be expected. It is believed that one reason for this may be that the majority of the resin is contained away from the surfaces of the foam sheet, thereby resulting in less tack at the surfaces. Hence, the polyurethane resin impregnated foam articles of the present invention already have reduced tack, and a tack reducing agent need not necessarily be employed.

The polyurethane prepolymer resin of the present invention also preferably contains a catalyst to control the set time and cure time of the resin. To produce suitable orthopedic splint devices in accordance with the present invention, a set time of about 3-18 minutes following activation of the polyurethane resin by dipping in water is preferred, with the most preferable set time being about 4-10 minutes. Suitable catalysts for moisture curing polyurethane prepolymer resin systems are well known. For example, tertiary amine catalysts such as 2,2'-dimorpholinodiethylether (DMDEE) described in U.S. Pat. No. 4,433,580 and 4-[2-[1-methyl-2-(4-morpholinyl)ethoxy]ethyl]-morpholine (MEMPE) described in commonly assigned, copending application Ser. No. 784,344, filed Oct. 4, 1985 (now U.S. Pat. No. 4,705,840), in amounts ranging from about 0.5% to about 5% by weight of the resin system, may be used for this purpose.

The resin impregnated foam sheets of the present invention are preferably prepared in a relatively low humidity chamber and sealed within a water vapor impermeable package. This package is opened just prior to application of the orthopedic article. Using such a system, the resin impregnated foam sheets of the present invention are relatively storage stable.

Optional elements of the orthopedic splinting articles of the present invention and one presently preferred method by which orthopedic splints can be formed in accordance with the present invention will now be described with reference to FIGS. 1, 2A, 2B, and 3. Referring first to FIG. 1, the orthopedic splinting article 10 is sized according to the forearm of the patient, and may be trimmed prior to application in order to provide a more exact fit. The thumbhole 12 may be formed by either punching or cutting out a corresponding portion of article 10.

Before actually applying article 10 to the forearm, a flexible stockinet or cast padding 14 is preferably placed around the patient's forearm so as to prevent undesirable adhesion or contact between the splint and forearm of the patient. For example, a tubular padding material, such as one side lofted tubular fabric made on an athletic sock machine available from Broadway Knitting Mills, 2152 Sacramento Street, Los Angeles, Calif. 90021, may be used for this purpose.

The splint of FIGS. 2A, 2B, and 3 is formed by first activating the resin of article 10 of FIG. 1 with water. Next, the left or right hand thumb of the patient is passed through aperture 12, and the long edge of the rectangular article is longitudinally aligned with the patient's forearm. The article is then circumferentially molded or positioned around the forearm to the position shown in FIGS. 2A and 2B. In this regard, the resin impregnated foam has excellent compression moldability or conformability to provide a good fit around the patient's forearm.

The article 10 is sufficiently dimensioned in its longest direction to extend the length of the forearm to be immobilized by the splint. The article 10 is dimensioned in the other direction so as to accommodate swelling of the forearm. This is preferably done by configuring article 10 so that it extends partially, but not completely, around the circumference of the forearm. In this regard, in order to accommodate the swelling of the forearm, the orthopedic splint 10 preferably extends around about 40% to about 90% of the circumference of the forearm, and most preferably around about 60% to about 75% of the circumference of the forearm. Such partial enclosure allows for swelling of the injured forearm, yet provides adequate immobilization thereof to promote healing.

However, it will be appreciated that the splinting article could also be configured in the circumferential direction so as to completely surround the forearm if desired. In order to accommodate swelling in such an instance, it is important that there remain a longitudinal break in the splinting article. Thus, although not the presently preferred embodiments, the splinting article could be merely wrapped around the forearm until the longest edges come into close proximity or even meet (without sealing the edges), or alternatively, so that the longest edges actually overlap slightly, but again without sealing the edges together so that the splint could still expand to accommodate swelling. Means to prevent sealing of the edges include the use of a nonadhering layer inserted between overlapping edges.

It should be noted that the accommodation of swelling involves at least two considerations. First, the orthopedic splint must provide for the accommodation of the swelling tissue itself. Second, the orthopedic splint should also be capable of manual expansion if necessary to accommodate even further swelling of the tissue. Thus, although the splint must be sufficiently rigid to immobilize the injured limb, it is desirable that the splint not be so rigid that some manual expansion is not possible when needed. The orthopedic splints of the present invention exhibit such properties.

The orthopedic splinting article 10 is preferably held in place while the resin is curing by the aid of securing means. For example, wrapping means such as a stretch bandage 16 shown in FIG. 3 may be used to secure article 10 around the forearm during curing so that the resultant orthopedic splint will conform well to the forearm. Although a right arm is shown in FIGS. 2A, 2B, and 3, it will be understood that the splinting article 10 may be applied equally well to a left arm.

After application, article 10 can be easily adjusted or repositioned during curing (but prior to setting of the resin) without substantial wrinkling. Furthermore, after curing and after the splint has served its intended purpose, the splint can be removed from the patient's forearm by unwrapping the stretch bandage and then prying open the splint. The general U-shape of forearm splint 10 shown in FIGS. 2A and 2B has been found to exhibit excellent strength and resistance to breakage.

In summary, the orthopedic splinting article 10 of the present invention can be applied to a forearm by: (1) exposing the article to water to initiate hardening of the resin, (2) manually squeezing out excess water, (3) properly positioning the orthopedic splinting article over a stockinet or cast pad applied to the forearm, (4) trimming the orthopedic splint to the desired shape, and (5) holding the splint in place as the resin cures, e.g., by wrapping a stretch bandage or other securing means around the splint article and forearm to secure the splint in place.

Figures 4, 5:
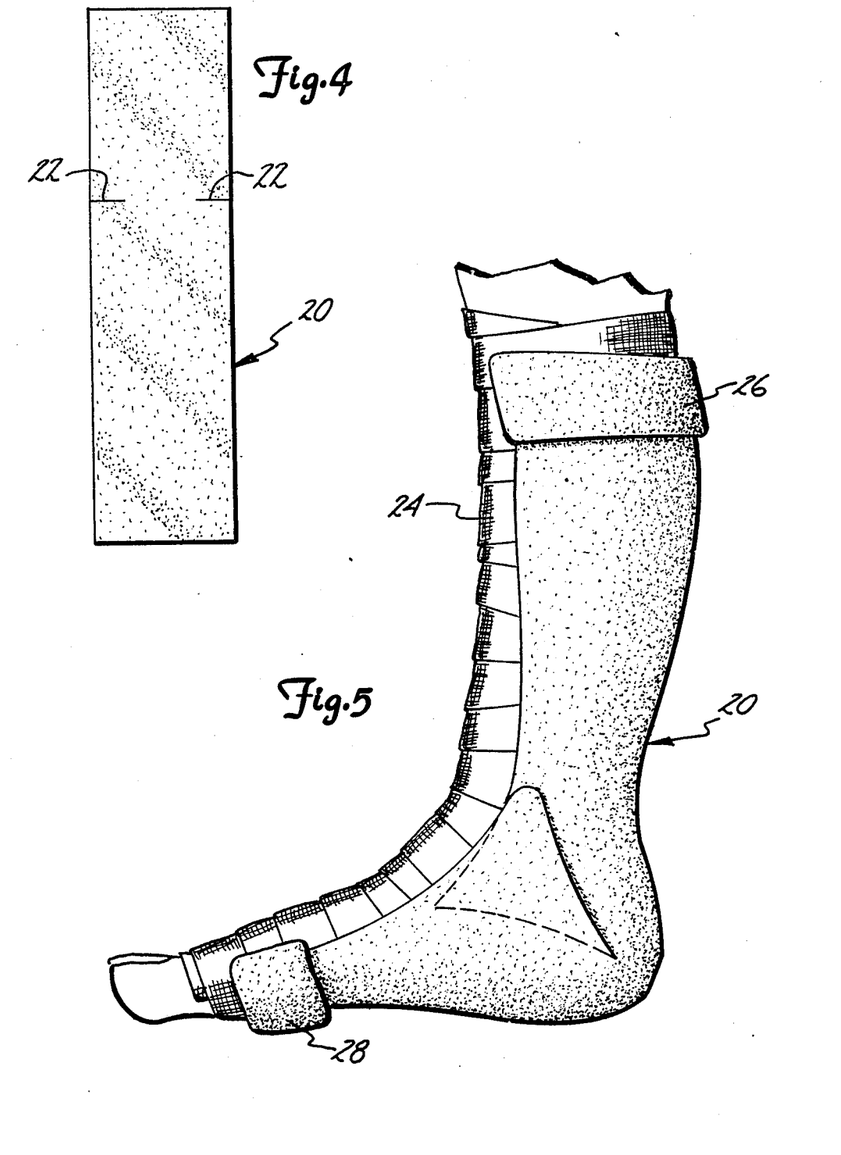
FIG. 4 is a plan view of a preferred lower leg embodiment of the orthopedic splinting article of the present inveniton prior to application.
FIG. 5 is a perspective view of the orthopedic splinting article of FIG. 4 formed into a lower leg splint.

The lower leg embodiment of the splinting article of the present invention will now be explained with reference to FIGS. 4 and 5. The lower leg splinting article 20 of FIGS. 4 and 5 is generally comprised of a unitary blank which has the same composition and characteristics of blank 10 used in the forearm application. Hence, the disclosure herein relating to forearm article 10 and the method of FIGS. 1-3 relates also to lower leg article 20 and the method of FIGS. 4-5, with the basic exception that lower leg article 20 is dimensioned somewhat larger in order to partially enclose the lower leg of the patient. Preferably, a cast padding 24 is also used between lower leg splint 20 and the patient's lower leg.

To facilitate application of splint 20, two slits 22 are preferably formed in splint 20 which, as shown best in FIG. 5, allow for some overlapping of the material to form an ankle and heel pocket in the splint around the patient's ankle and heel, and thereby avoid bulky material folds which would otherwise be experienced without such slits. These slits 22 are preferably formed by the physician applying the lower leg splint so that the splint can be precisely tailored to the particular patient's leg size. Furthermore, it may be desirable to fold the foam material over at the patient's calf to form a fold 26 or at the patient's toes to form a fold 28 so as to customize lower leg splint 20 to the appropriate proportions of the patient's lower leg. Additionally, fold 28 provides additional strength at the extremities of the splint 20 where weight bearing characteristics become more important. Although not shown in FIG. 5, a stretch bandage or other securing means should also be applied around lower leg splint 20 so as to secure the splint in place and to provide better conformability to the lower leg during curing.

It will be understood that various modifications and changes may be made by those skilled in the art to accommodate different situations. For example, a simple cylindrical splint may be formed in accordance with the present invention so as to immobilize an upper or lower arm, an upper or lower leg, or even a knee. By a cylindrical splint article, it is meant that the article does not necessarily include a thumbhole or heel pocket, etc.

The present invention will be further understood in view of the following examples which are merely illustrative and are not to be considered as comprehensive or limiting in any way.

EXAMPLE 1

In this example, a forearm splint within the scope of the present invention was prepared. First, a polyether based polyurethane foam, having a thickness of ½ inch, was procured from Illbruck USA as Type E-150. This foam material has a density of about $1.5 \pm 0.1$ lbs/ft$^3$, and a pore size of about 60 pores per lineal inch. A 7 inch by 12 inch sheet of this foam material was cut, and a thumb hole was placed in the material in the approximate position shown in FIG. 1. The weight of the foam sheet was determined to be about 22 grams, and this figure was used to determine the correct amount in grams of the resin to be used in order to achieve a resin loading of about 85% by weight of the final resin impregnated foam sheet.

A polyurethane prepolymer resin having an NCO:OH ratio of about 3.0:1 was prepared as follows. In an atmosphere maintained at about 4% relative humidity, a vessel was charged with about 396 grams of MRS-10 obtained from Mobay Chemical. (This isocyanate compound has an NCO equivalent weight of about 132 grams of isocyanate per NCO group.) A second vessel was charged with about 342 grams of castor oil as the polyol, which was obtained from Caschem. (The castor oil had an OH equivalent weight of about 342 grams of polyol per OH group.) To the castor oil in the second vessel was added about 0.74 grams of benzoylchloride, and about 9 grams of 4-[2; -[1-methyl-2-(4-morpholinyl)ethoxy]-ethyl]-morpholine (MEMPE) prepared as described in copending application Ser. No. 784,344, filed Oct. 4, 1985. The mixture in the second vessel was then added to the isocyanate compound contained in the first vessel, and the components were blended together. (This prepolymer mixture had an NCO equivalent weight of about 374 grams of prepolymer mixture per NCO group.) Immediately after blending these components together, the blended resin mixture was impregnated into the foam sheet in an amount such that the resin represented about 85% by weight of the final product. Such impregnation of the resin into the foam sheet was achieved in a moisture-free chamber by spreading the resin over all surfaces of the foam sheet and then manually kneading the resin into the foam material. The viscosity of the polyurethane resin, after reaction of the components, was determined to be about 200,000 centipoise. The splint article thus prepared was then sealed in an air-tight pouch to protect the article from exposure to moisture.

Later, the forearm splint article prepared in this Example 1 was applied to a human forearm using the following procedure. First, a conventional cast padding was wrapped around the forearm. Next, the splint article was removed from the air-tight pouch and trimmed to more precisely fit the forearm. The article was then submerged in water and squeezed several times in order to ensure proper activation of the resin, lifted out of the water, and excess water was squeezed out. The article was then placed around the forearm to provide a good fit. In order to hold the splint in place during curing and provide better conformability and moldability to the forearm, a stretch bandage was wrapped around the splint article immediately after placing the article around the forearm. The splint article extended about 75% around the forearm and the exotherm was such that a temperature (measured by thermocouples inserted next to the skin) of about 40° C. was observed during curing. After about 5 minutes from the initial water activation of the resin, the splint was sufficiently rigid to support the forearm. There was no apparent moisture or dampness retained against the surface of the skin under the cured splint.

EXAMPLE 2

In this example, a forearm splint within the scope of the present invention was prepared and applied to a human forearm in accordance with the procedure of Example 1 with the following exceptions. In this Example 2, a polyurethane prepolymer resin having an NCO-:OH ratio of about 2.5:1 was prepared by charging the first vessel with about 360 grams of Isonate® 143L obtained from Upjohn. The second vessel was charged with about 216 grams of Niax® polyol PPG 425 obtained from Union Carbide, about 0.58 grams of benzoylchloride, and about 7 grams of MEMPE catalyst. Thus, in this example, the prepolymer resin represented about 80% by weight of the final product, and the prepolymer resin had an NCO equivalent weight of about 388 grams of prepolymer resin per NCO group. The prepolymer resin, before moisture curing, had a measured viscosity in excess of 200,000 centipoise. The temperature which would be felt by the patient during curing was measured to be about 39° C. The forearm splint formed in this example was found to be efficacious and was sufficiently set after about 5 minutes from the initial activation of the prepolymer resin.

EXAMPLE 3

In this example, a lower leg splint within the scope of the present invention was prepared and applied to a lower leg in accordance with the procedure of Example 1 with the following exceptions. For this lower leg application, a foam sheet was cut from the ½ inch foam material having dimensions of about 10 inches by about 38 inches. A slit about 3 inches long was cut into each 38 inch edge about 12 inches from the end of the foam sheet similarly to slits 22 shown in FIG. 4. The lower leg splint article prepared was then applied around a human lower leg and the material adjacent the slits was overlapped as shown in FIG. 5 so as to form an ankle/heel pocket. The curing time, exotherm observed, and other data observed were the same in this Example 3 as in Example 1 above.

EXAMPLES 4 and 5

In these examples, orthopedic splinting materials within the scope of the present invention were prepared in order to show the relative rigidity of the materials. In Examples 4 and 5, the orthopedic splinting materials were not applied to any limb, but were rather tested for their elongation after curing. The materials of Examples 4 and 5 were prepared in accordance with the procedure of Example 1, with the following acceptions. In both Examples 4 and 5, a polyurethane prepolymer resin having an NCO:OH ratio of about 3 to 1 was prepared by charging the first vessel with about 432 grams of 143L obtained from Upjohn. The second vessel was charged with about 216 grams of Niax® polyol PPG 425 obtained from Union Carbide, about 0.65 grams of benzoylchloride, and about 8 grams of MEMPE catalyst. Further, the foam materials used in Examples 4 and 5 were a 4"×8"×½" piece of P-100 foam (having 100 pores per inch) available from Illbruck U.S.A., Minneapolis, Minn., and a 4"×8"×½" piece of P-45NR foam (having 45 pores per inch) available from Illbruck U.S.A., respectively. In Example 4, enough of the prepolymer resin was impregnated into the P-100 foam such that the prepolymer resin represented about 80% by weight of the final product. In Example 5, enough prepolymer resin was impregnated into the P-45NR foam such that the prepolymer resin represented about 85% by weight of the final product. Each resin impregnated foam sheet was placed in a foil pouch and sealed.

Later, the resin impregnated foam sheets were removed from their respective foil pouches, dipped in water to activate the prepolymer resin, and allowed to cure for several days. During curing of the resin impregnated foam sheet of Example 4, the foam was compressed to about ½ of its normal thickness (i.e., compressed to about ¼") during cure so as to simulate the compression which would typically occur when wrapping the material around an injured body part.

After curing was complete, each of the cured sheets was cut into six strips which measured ½ inch wide and 4 inches long. Each of these strips was then tested for maximum elongation before breaking. For this purpose, each cured strip was mounted in pneumatic grips which were attached to a TTM Table Model Instron apparatus equipped with a 50 kilogram load cell. The test conditions were set as follows:

Chart Rate=50 cm/min
Crosshead Rate=5.0 cm/min
Gauge Length=5.0 cm/min

Each of the sample strips was elongated until it broke. The ultimate elongation for each of the strips tested in Examples 4 and 5 was measured to be less than 1.5% of the original strip length. Hence, Examples 4 and 5 evidence the relative rigidity of the resin impregnated foam sheets of the present invention after curing has been completed.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. An article suitable for forming an orthopedic splint around at least a portion of an animal body part, comprising:
   a unitary blank dimensioned in a first direction sufficient to extend the length of said body part and dimensioned in a second direction sufficient to extend at least partially around the circumference of said body part, said unitary blank being packaged as an orthopedic splinting material and comprising:
   an open-celled foam sheet; and
   a water curable, isocyanate functional, prepolymer resin impregnated into said open-celled foam sheet, said prepolymer resin being formed by reacting a polyisocyanate with a polyol wherein the ratio of NCO groups in said polyisocyanate to OH groups in said polyol is between about 2 to 1 and about 3.5 to about 1, said prepolymer resin having an NCO equivalent weight of from about 350 to about 1000 grams of prepolymer resin per NCO group, whereby upon activating said water curable prepolymer resin and applying said blank around said portion of said body part, said orthopedic splint is formed.

2. An article as defined in claim 1 wherein said prepolymer resin is formed by reacting said polyisocyanate with said polyol while said polyisocyanate and said polyol are inside said open-celled foam sheet.

3. An article as defined in claim 1 wherein said open-celled foam sheet has from about 30 to about 120 pores per inch.

4. An article as defined in claim 1 wherein said open-celled foam sheet has a density of from about 1 to about 4.5 lbs/ft³.

5. An article as defined in claim 1 wherein said prepolymer resin comprises from about 70% to about 95% by weight of said unitary blank.

6. An article as defined in claim 1 wherein, after reaction of said polyisocyanate and said polyol, said prepolymer resin has a viscosity of about 75,000 centipoise or greater.

7. An article as defined in claim 1 wherein said prepolymer resin has an NCO equivalent weight of from about 370 to about 600 grams of prepolymer resin per NCO group.

8. An article as defined in claim 1 wherein upon curing said prepolymer resin, a temperature of about 48° C. or less is felt by the animal.

9. An article as defined in claim 1 wherein said unitary blank is dimensioned in said second direction so as to extend around about 40% to about 90% of the circumference of said body part.

10. An article as defined in claim 1 wherein said article further comprises a tack reducing agent.

11. An article as defined in claim 1 further comprising an extensible fabric positionable between said unitary blank and said body part.

12. An article as defined in claim 1 further comprising a cast pad positionable between said unitary blank and said body part.

13. An article as defined in claim 1 further comprising wrapping means for securing said unitary blank to said body part during curing so as to conform said unitary blank to said body part.

14. An article as defined in claim 1 wherein said prepolymer resin further comprises a catalyst and wherein said article is sealed within a water vapor impermeable package.

15. An article as defined in claim 1 wherein said open-celled foam sheet has a thickness of from about 5/16 of an inch to about ¾ of an inch.

16. An article suitable for forming an orthopedic splint around at least a portion of an animal body part, comprising:
   a unitary blank dimensioned in a first direction sufficient to extend the length of said body part and dimensioned in a second direction sufficient to extend at least partially around the circumference of said body part, said blank comprising:
   an open-celled foam sheet having from about 45 to about 100 pores per inch and having a density of from about 1 to about 3 lbs/ft³; and
   a water curable, isocyanate functional, polyurethane resin impregnated into said open-celled foam sheet in sufficient quantity such that said polyurethane resin comprises from about 70% to about 95% by weight of said unitary blank, said polyurethane resin being formed by reacting a polyisocyanate with a polyol while said polyisocyanate and said polyol are inside said open-celled foam sheet, the ratio of NCO groups in said polyisocyanate to OH groups in said polyol being between about 2.5 to 1 and about 3 to 1, said polyurethane resin having an NCO equivalent weight of from about 370 to about 600 grams of polyurethane resin per NCO group and a viscosity of about 100,000 centipoise or greater, whereby upon activating said water curable polyurethane resin and applying said blank around said portion of said body part, said orthopedic splint is formed.

17. An article as defined in claim 16 wherein said open-celled foam sheet has a thickness of from about 5/16 of an inch to about ¾ of an inch.

18. An article suitable for forming an orthopedic splint around at least a portion of an animal body part, comprising:
   a unitary blank dimensioned in a first direction sufficient to extend the length of said body part and dimensioned in a second direction sufficient to extend at least partially around the circumference of said body part, said unitary blank being packaged as an orthopedic splinting material and comprising:
   an open-celled foam sheet; and
   a water curable, isocyante functional, prepolymer resin impregnated into said open-celled foam sheet, said prepolymer resin being formed by reacting a polyisocyanate with a polyol, said prepolymer resin having an NCO equivalent weight of from about 350 to about 1000 grams of prepolymer resin per NCO group, said prepolymer resin having a viscosity of about 75,000 centipoise or greater after the reaction is complete, whereby upon activating said water curable prepolymer resin and applying said blank around said portion of said body part, said orthopedic splint is formed.

19. An article as defined in claim 18 wherein said open-celled foam sheet has a thickness of from about 5/16 of an inch to about ¾ of an inch.

20. An article as defined in claim 18 wherein said prepolymer resin is formed by reacting said polyisocyanate with said polyol while said polyisocyanate and said polyol are inside said open-celled foam sheet.

21. A method for forming an orthopedic splint around at least a portion of animal body part, comprising the steps of:
providing a unitary blank according to claim 1;
activating said prepolymer resin within said blank; and
applying said blank around said portion of said body part so as to conform said blank to said body part and form said orthopedic splint.

22. An article capable of being applied around at least a portion of an animal body part, comprising:
a unitary blank dimensioned in a first direction sufficient to extend the length of said animal body part and dimensioned in a second direction sufficient to extend at least partially around the circumference of said animal body part, said blank comprising:
an open-celled foam sheet; and
a water curable, isocyanate functional, prepolymer resin impregnated into said open-celled foam sheet, said prepolymer resin being formed by reacting a polyisocyanate with a polyol while said polyisocyanate and said polyol are inside said open-celled foam sheet, wherein the ratio of NCO groups in said polyisocyanate to OH groups in said polyol is between about 2 to 1 and about 3.5 to 1, said prepolymer resin having an NCO equivalent weight of from about 350 to about 1000 grams of prepolymer resin per NCO group, whereby upon activating said water curable prepolymer resin and applying said blank around said portion of said animal body part, said blank becomes rigid.

23. An article as defined in claim 22 wherein said open-celled foam sheet has a thickness of from about 5/16 of an inch to about ¾ of an inch.

24. An article suitable for forming an orthopedic splint around at least a portion of an animal body part, comprising:
a unitary blank dimensioned in a first direction sufficient to extend the length of said body part and dimensioned in a second direction sufficient to extend at least partially around the circumference of said body part, said blank comprising:
an open-celled foam sheet; and
a water curable, isocyanate functional, prepolymer resin impregnated into said open-celled foam sheet, said prepolymer resin being formed by reacting a polyisocyanate with a polyol while said polyisocyanate and said polyol are inside said open-celled foam sheet, wherein the ratio of NCO groups in said polyisocyanate to OH groups in said polyol is between about 2 to 1 and about 3.5 to 1, said prepolymer resin having an NCO equivalent weight of from about 350 to about 1000 grams of prepolymer resin per NCO group, whereby upon activating said water curable prepolymer resin and applying said blank around said portion of said body part, said orthopedic splint is formed.

25. An article as defined in claim 24 wherein said open-celled foam sheet has a thickness of from about 5/16 of an inch to about ¾ of an inch.

26. An article suitable for forming an orthopedic splint around at least a portion of an animal body part, comprising:
a unitary blank dimensioned in a first direction sufficient to extend the length of said body part and dimensioned in a second direction sufficient to extend at least partially around the circumference of said body part, said blank comprising:
an open-celled foam sheet; and
a water curable, isocyanate functional, prepolymer resin impregnated into said open-celled foam sheet, said prepolymer resin being formed by reacting a polyisocyanate with a polyol while said polyisocyanate and said polyol are inside said open-celled foam sheet, whereby upon activating said water curable prepolymer resin and applying said blank around said portion of said body part, said orthopedic splint is formed.

27. An article as defined in claim 26 wherein said open-celled foam sheet has a thickness of from about 5/16 of an inch to about ¾ of an inch.

28. A method of preparing a unitary blank suitable for use in forming an orthopedic splint around at least a portion of an animal body part, said method comprising the steps of:
providing an open-celled foam sheet dimensioned in a first direction sufficient to extend the length of said body part and dimensioned in a second direction sufficient to extend at least partially around the circumference of said body part; and
impregnating said open-celled foam sheet with a water curable, isocyanate functional, prepolymer resin formed by reacting a polyisocyanate with a polyol, the ratio of NCO groups in said polyisocyanate to OH groups in said polyol being between about 2 to 1 and about 3.5 to 1, said prepolymer resin having an NCO equivalent weight of from about 350 to about 1000 grams of prepolymer resin per NCO group, said resin-impregnated foam sheet being a unitary blank which is packaged at an orthopedic splinting material.

29. A method as defined in claim 28 wherein said open-celled foam sheet has a thickness of from about 5/16 of an inch to about ¾ of an inch.

30. A method as defined in claim 28 wherein said polyisocyanate and said polyol are reacted within said foam sheet to form said prepolymer resin in situ.

31. A method as defined in claim 28 wherein said open-celled foam sheet has from about 30 to about 120 pores per inch.

32. A method as defined in claim 28 wherein said open-celled foam sheet has a density of from about 1 to about 4.5 lbs./ft$^3$.

33. A method as defined in claim 28 wherein said prepolymer resin comprises from about 70% to about 95% by weight of said article.

34. A method as defined in claim 28 wherein after reaction of said polyisocyanate and said polyol, said prepolymer resin has a viscosity of about 75,000 centipoise or greater.

35. A method as defined in claim 28 wherein said prepolymer resin has an NCO equivalent weight of from about 370 to about 600 grams of prepolymer resin per NCO group.

* * * * *

UNITED STATES PATENT AND TRADEMARK OFFICE
CERTIFICATE OF CORRECTION

PATENT NO. : 4,946,726
DATED      : August 7, 1990
INVENTOR(S): Timothy C. Sandvig et al.

It is certified that error appears in the above-identified patent and that said Letters Patent is hereby corrected as shown below:

Cover page, right column, line 29, "Husle" should be --Hulse--.
Col. 1,  line 8,  after "Method" insert --"--.
Col. 1,  line 9,  after "4,683,877)" delete the quotation mark.
Col. 4,  line 42, after "4,683,877)" insert --. For example, the--.
Col. 9,  line 32, "ASTM-D-)1894," should be --ASTM-D-1894,--.
Col. 9,  line 34, after "foil." insert --)--.
Col. 12, line 49, after "of" insert --Mondur®--.
Col. 12, line 58, "4-[2;-[" should be --4-[2-[--.
Col. 14, line 16, "acceptions" should be --exceptions--.
Col. 14, line 20, after "of" insert --Isonate®--.
Col. 15, line 25, "to about 1" should be --to 1--.
Col. 16, line 57, "isocyante" should be --isocyanate--.
Col. 17, line 9,  before "animal" insert --an--.
Col. 18, line 60, after "wherein" insert --,--.

Signed and Sealed this

Twenty-second Day of October, 1991

Attest:

HARRY F. MANBECK, JR.

*Attesting Officer*    *Commissioner of Patents and Trademarks*